(12) United States Patent
Kwon et al.

(10) Patent No.: US 8,119,595 B2
(45) Date of Patent: Feb. 21, 2012

(54) STABLE, AQUEOUS SOLUTION OF HUMAN ERYTHROPOIETIN, NOT CONTAINING SERUM ALBUMIN

(75) Inventors: Kyu Chan Kwon, Seoul (KR); Suk Young Choi, Daejeon (KR); Young Cheol Kang, Daejeon (KR); Hoon Sung Jeh, Daejeon (KR); Seung Joo Lee, Daejeon (KR); Myung Jin Kim, Daejeon (KR); Ji Eon Kim, Daejeon (KR); Jin-Seok Oh, Daejeon (KR)

(73) Assignee: LG Life Sciences, Ltd. (KR)

( * ) Notice: Subject to any disclaimer, the term of this patent is extended or adjusted under 35 U.S.C. 154(b) by 854 days.

(21) Appl. No.: 10/560,374

(22) PCT Filed: Jun. 7, 2004

(86) PCT No.: PCT/KR2004/001358
§ 371 (c)(1),
(2), (4) Date: Mar. 29, 2007

(87) PCT Pub. No.: WO2004/108152
PCT Pub. Date: Dec. 16, 2004

(65) Prior Publication Data
US 2007/0293419 A1    Dec. 20, 2007

(30) Foreign Application Priority Data
Jun. 10, 2003 (KR) .................. 10-2003-0037060

(51) Int. Cl.
*A61K 38/18* (2006.01)
(52) U.S. Cl. ........................................... 514/7.7
(58) Field of Classification Search .................. None
See application file for complete search history.

(56) References Cited

U.S. PATENT DOCUMENTS

| | | | | |
|---|---|---|---|---|
| 4,806,524 | A | 2/1989 | Kawaguchi et al. | 514/8 |
| 4,879,272 | A | 11/1989 | Shimoda et al. | 514/8 |
| 4,992,419 | A | 2/1991 | Woog et al. | 514/8 |
| 5,376,632 | A | 12/1994 | Konings et al. | 514/8 |
| 5,661,125 | A | 8/1997 | Strickland | 514/8 |
| 6,303,113 | B1 | 10/2001 | Woog et al. | 424/85.1 |
| 6,867,182 | B2 * | 3/2005 | Papadimitriou | 514/2 |
| 2002/0037841 | A1 | 3/2002 | Papadimitriou | 514/8 |

FOREIGN PATENT DOCUMENTS

| | | |
|---|---|---|
| EP | 0909564 | 4/1999 |
| WO | 85/02610 | 6/1985 |
| WO | 00/61169 | 10/2000 |
| WO | 01/87329 | 11/2001 |
| WO | WO 2004/006958 * | 1/2004 |

OTHER PUBLICATIONS

"Instability, Stabilization, and Formulation of Liquid Protein Pharmaceuticals"; Author: Wei Wang; International Journal of Pharmaceutics; 185, 129-188, 1999.
"Correction of the Anemia of End-Stage Renal Disease With Recombinant Human Erythropoietin"; Author: Eschbach, et al.; New England J. Med. vol. 316,No. 2; 73-78; 1987.
Overview of the Stability and Handling of Recombinant Protein Drugs; Author: John Giegert; Journal of Parenteral Science & Technology, vol. 43, No. 5; 220-224, 1989.
"Blood"; Author: Sanford B.K.; Journal of the American Society of Hematology, vol. 77, No. 3; 419-434, 1991.
"Influence of Surfactants Upon Protein/Peptide Adsorption to Glass and Polyprophlene"; Author: Duncan, et al.; Int. J. Pharm.; 120; 179-188, 1995.
"Purification of Human Erythropoietin" Author: Miyake, et al.; J. Bol. Chem. vol. 252; No. 15; 5558-5564, 1997.
"Adsorption of Protiens From Solution At the Solid-Liquid Interface"; Author: Willem Norde; Adv. Colloid Interface Sci. vol. 25; 267-341, 1986.
"Pharmaceutical Excipients for the Stabilization of Proteins"; Author: David Wong,et al.; Pharm. Tech.; 34-50; Oct. 1997.

* cited by examiner

*Primary Examiner* — Elizabeth C Kemmerer
*Assistant Examiner* — Regina M Deberry
(74) *Attorney, Agent, or Firm* — Cantor Colburn LLP

(57) ABSTRACT

The present invention provides an aqueous formulation of human erythropoietin having the storage stability over a long period without serum albumin, in which the formulation comprises a pharmaceutically effective amount of human erythropoietin; non-ionic surfactant, polyhydric alcohol, neutral amino acid and sugar alcohol as stabilizers; isotonic reagent; and buffering reagent.

9 Claims, No Drawings

STABLE, AQUEOUS SOLUTION OF HUMAN ERYTHROPOIETIN, NOT CONTAINING SERUM ALBUMIN

FIELD OF THE INVENTION

The present invention relates to an aqueous formulation of human erythropoietin having the storage stability over a long period without serum albumin. More specifically, the present invention relates to the formulation comprising a pharmaceutically effective amount of human erythropoietin; non-ionic surfactant, polyhydric alcohol, neutral amino acid and sugar alcohol as stabilizers; isotonic reagent; and buffering reagent.

BACKGROUND OF THE INVENTION

Erythropoietin (EPO) is a glycoprotein which induces production of erythrocytes in the bone marrow by stimulating differentiation of erythroid progenitor cells. EPO consists of 165 amino acids. After purification of erythropoietin from human urine by Mijake in 1977, it has become possible to produce large amounts by genetic engineering technology. Erythropoietin was found to be able to induce effectively various hematopoiesis in the treatment of anemia resulting from a chronic renal insufficiency and various types of anemia by several causes, and in use during certain surgical procedures (Mijake et al., *J. Biol. Chem.* 25, 5558-5564, 1977; Eschbach et al., *New Engl. J. Med.* 316, 73-78, 1987; Sandford. B. K, *Blood,* 177, 419-434, 1991; WO 85-02610). For this reason, erythropoietin has been used as a pharmaceutical in various indications of diseases for a long time. However, like other protein pharmaceuticals, erythropoietin protein should also be carefully prepared to prevent denaturation from being caused by the loss of stability, for the purpose of the effective usage thereof.

Generally, proteins have a short half-life and denaturation easily occurs such as by aggregation of monomers, precipitation by aggregation, and adsorption to ampoule walls when exposed to extreme temperatures, interface of water and air, high pressure, physical and mechanical stresses, organic solvents, contamination by microorganisms and the like. Denatured proteins lose their native physiochemical properties and physiological activity, and the denaturation of protein is generally irreversible. Thus, proteins cannot recover their native properties, once denatured. Especially, in case of proteins such as erythropoietin, which is administered in single dosages as small as a few micrograms, when they are adsorbed to the ampoule wall due to the disappearance of stability, the loss resulting therefrom is relatively considerable. Furthermore, the protein thus adsorbed easily aggregates via a denaturation process, and administration of the denatured protein causes antibodies, as spontaneously produced proteins, to be formed against this denatured protein in a body, thus the protein should be administered in the substantially stable form. Accordingly, various methods to prevent protein denaturation in aqueous solution have been studied (John Geigert, *J. Parenteral Sci. Tech.,* 43, No5, 220-224, 1989; David Wong, *Pharm. Tech.* October, 34-48, 1997; Wei Wang, *Int. J. Pharm.,* 1 85, 129-188, 1999; Willem Norde, *Adv. Colloid Interface Sci.,* 25, 267-340, 1986; Michelle et al., *Int. J. Pharm.* 120, 179-188, 1995).

Some protein formulations solved the denaturation with a lyophilization method. However, lyophilized products are inconvenient since they have to be reconstituted prior to injection, and a large capacity freeze-dryer is required for processing, therefore, extensive investment is necessary. A method of producing powdered forms of protein using spray-drying techniques is also used; however, it has disadvantages in that the economic efficiency decreases due to low yield and exposure to high temperature can cause protein denaturation during the process.

As an alternative way to solve the limitation of the above methods, there is a method to improve the protein stability by adding stabilizers to an aqueous protein solution. As protein stabilizers, there are known surfactants, serum albumin, polysaccharides, amino acids, macromolecules and salts (John Geigert, *J. Parenteral Sci. Tech.,* 43, No. 5, 220-224, 1989; David Wong, *Pharm. Tech.*, October, 34-48, 1997; Wei Wang., *Int. J. Pharm.,* 185, 129-188, 1999). However, suitable stabilizers should be selected in accordance with physiochemical characteristics of each protein; otherwise, for example, when stabilizers are used in certain combinations, competitive reaction or side reaction can occur to result in negative effects different from the intended effects. Moreover, since an appropriate range of concentrations exists for each stabilizer, much effort and caution are needed to stabilize aqueous proteins (Wei Wang, *Int. J. Pharm.,* 185, 129-188, 1999).

Among the protein stabilizers, serum albumin and gelatin, derived from human or animal, are generally used as stabilizers of aqueous protein formulations and have been proven to be effective. However, there is a risk of viral contamination with human-derived serum albumin, and gelatin and bovine serum albumin may transmit diseases like "Transmissible Spongiform Encephalopathies", or raise allergies in some patients; therefore, in Europe, use of materials from human and animal sources as pharmaceutical additives is increasingly restricted (EMEA/CPMP/BWP/450/01 Report from the Expert Workshop on Human TSEs and Medicinal products derived from Human Blood and Plasma (1 Dec. 2000), CPMP/PS/201/98 Position Statement on New Variant CJD and Plasma-Derived Medicinal Products (Superseded by CPMP/BWP/2879/02). Thus, it is necessary to develop methods of formulating stable protein formulations without serum albumin from human or animal, solving the problems of existing erythropoietin formulations containing serum albumin.

In U.S. Pat. No. 4,879,272, there is disclosed the addition of human/bovine serum albumin, lecithin, dextran and cellulose as agents to inhibit protein adherence to ampoule walls. According to this patent, the recovery yield of erythropoietin is good at 69~98% after storage for about 2 hours at 20° C., compared with only 16% without such an addition, but it has a problem that the loss due to adsorption can be considerable.

In U.S. Pat. No. 4,806,524, there are disclosed the lyophilized formulation and aqueous formulation of erythropoietin, using polyethylene glycol, protein, saccharides, amino acids, organic salts and inorganic salts as stabilizers for erythropoietin. According to this patent, after storage of about 7 days at 25° C., the lyophilized formulation has a high recovery yield level of 87~98%, but the aqueous formulation has a low recovery yield level of only 60~70%, thus the aqueous formulation is relatively less stable.

In U.S. Pat. No. 4,992,419, there are disclosed the aqueous formulation and lyophilized formulation of erythropoietin, in which 0.5~5 g/L of non-ionic surfactant as an anti-absorption agent, and 5~50 g/L of urea and 5~25 g/L of amino acids as stabilizers were used. However, this patent has problems that the aqueous formulation shows a limited stability compared to the formulations containing human serum albumin, and the lyophilized formulation requires the reconstitution process so as to maintain a sufficient activity.

In U.S. Pat. No. 5,376,632, there are disclosed the aqueous formulation, lyophilized formulation and spray-dried powder formulation of erythropoietin, containing β or γ cyclodextrins but not containing other additional pharmaceutical excipient. However, the formations using cyclodextrins are not practical due to their renal toxicity.

In U.S. Pat. No. 5,661,125, there are disclosed the formation of erythropoietin, containing benzyl alcohol, parabens, phenol and mixtures thereof, and an experiment showing the stability thereof compared to the formation of erythropoietin containing human serum albumin. However, the formulation of this patent showed a low stability and significant precipitation of erythropoietin even at low temperature.

In WO 01/87329 A1, there are disclosed the aqueous formulations of erythropoietin and a multiple charged inorganic anion in a pharmaceutically acceptable buffer to keep the solution pH in the range from about pH 5.5 to about pH 7.0. This application shows the comparative experiment regarding stability in which, after storage of EPO and PEGylated EPO at various temperatures for 6 months, the content of sialic acid and the standard bioactivity (%) of each EPO were measured in various formulations; however, since the amount of EPO monomers was not measured, the recovery yield (%) of EPO monomers cannot be precisely determined.

Therefore, it is desired to provide the new aqueous formulation that has a long-term stability without using protein components derived from animal such as serum albumin.

SUMMARY OF THE INVENTION

The object of the present invention is to provide an aqueous formulation of erythropoietin which can maintain its biological activity over a long period in vivo without using serum albumin derived from human or animal.

Through many experiments and intensive studies, the inventor found an aqueous formulation of human erythropoietin preventing adhesion to the ampoule wall and protein denaturation, occurring upon storage for long periods, when a pharmaceutically effective amount of erythropoietin was combined with specific components as stabilizers, isotonic reagent and buffer reagent, and accomplished the invention.

DETAILED DESCRIPTION OF THE INVENTION

Therefore, the present invention provides the aqueous formulation of human erythropoietin comprising a pharmaceutically effective amount of human erythropoietin; non-ionic surfactant, polyhydric alcohol, neutral amino acids, sugar alcohol as stabilizers; isotonic reagent; and buffering reagent.

The human erythropoietin, which can be used in the aqueous formulation of the present invention, includes every types of erythropoietin obtainable by isolation and purification from animal cells by native and/or genetic recombinant method. The amount of the erythropoietin in the aqueous formulation is preferably 100 IU/ml to 120,000 IU/ml.

The aqueous formulation of the present invention contains the non-ionic surfactant to stabilize the formulation, thereby preventing adhesion to ampoule walls, in which the non-ionic surfactant decrease the surface tension of proteins to prevent adhesion or aggregation of the proteins on the hydrophobic surfaces. The preferable example of non-ionic surfactant for use in the present invention includes polysorbate-based and poloxamer-based non-ionic surfactants, and they can be used alone or in combination of two or more thereof. Among them, polysorbate-based non-ionic surfactants are more preferable. The example of these polysorbate-based non-ionic surfactants includes polysorbate 20, polysorbate 40, polysorbate 60 and polysorbate 80, and among them, polysorbate 20 is particularly preferable. Polysorbate 20 inhibits chemical degradation of protein, as well as decreasing or preventing the adhesion of proteins at low concentration, because its Critical Micelle Concentration is relatively low. The use of high concentrations of the non-ionic surfactant in an aqueous formulation is not preferable because such concentration causes interference with UV-spectroscopy and Isoelectric Focusing in examining the stability and concentration of protein, so that it is difficult to evaluate protein stability. Therefore, in the aqueous formulation of the present invention, the non-ionic surfactant is preferably incorporated in amounts of less than 0.01%, more preferably 0.0001 to 0.01% (w/v).

The neutral amino acid allows more many water molecules to be present around erythropoietin so that the outermost hydrophilic amino acids of the erythropoietin can be stabilized, thereby stabilizing the erythropoietin itself (Wang, Int. J. Pharm. 185 (1999) 129-188). Since charged amino acids can facilitate aggregation of erythropoietin by electrostatic interaction, the neutral amino acid is used in the aqueous formulation of the present invention. The preferable example of neutral amino acid, which can be used in the present invention, includes glycine, alanine, leucine, isoleucine, etc., and among them, glycine is more preferable. These neutral amino acid can be used alone or in combination with two or more; however, according to the experiments conducted by the inventors of the present invention, glycine is more effective when it is used alone than in combination with other amino acids. However, the aqueous formulation of the present invention is not intended to be limited to using one kind of neutral amino acid. The amount of neutral amino acid for use in the present invention is preferably 0.001 to 2% (w/v). If the amount is below this range, there may be no effect of increasing stability. On the other hand, if the amount is above this range, high concentration of erythropoietin cannot be achieved due to the increased osmotic pressure influencing solubility of erythropoietin.

In the aqueous formulation of the present invention, the polyhydric alcohol is used as one of stabilizers for erythropoietin in the solution. The preferable example of polyhydric alcohol includes propylene glycol, polyethylene glycol of low molecular weight, glycerol, and polypropylene glycol of low molecular weight, and one or a combination of two or more thereof can be used. Especially among them, propylene glycol is more preferable. Propylene glycol has been broadly used in pharmaceuticals administered via parenteral or non-parenteral routes as a solvent of hydrophobic materials, extractant and preservative, and it is considered as non-toxic. Furthermore, it is used as an emulsifier or vehicle in foods and cosmetics. In addition to the above, it can also be used as a stabilizer of pharmaceuticals to increase the solubility of phospholipid when phospholipid is used as a stabilizer of the aqueous formulations. Propylene glycol can also be used to increase the stability of aqueous formulations of protein, and it generally improves further the stability of aqueous formulations when used in combination with other stabilizers of suitable concentrations than when used alone. However, it should be noted that the inventors of the present invention ascertained that, despite use of polypropylene glycol, the stability of aqueous formulation is unexpectedly decreased in case of not suitably selecting kinds and concentration ranges of other stabilizers which are used in combination with propylene glycol. The amount of polyhydric alcohol is preferably 0.0001 to 0.1% (w/v). If the amount is below this range, there may be no effect of increasing stability. On the other hand, if the amount is above this range, there may be a problem with an increased osmotic pressure.

The sugar alcohol, as one of stabilizers of the aqueous formulations of the present invention, plays a role to stabilize erythropoietin when supplied in solution with the non-ionic surfactant, neutral amino acid and polyhydric alcohol as mentioned above. The preferable example of the sugar alcohol includes mannitol, sorbitol, cyclitol, inositol, etc. which can be used alone or in combinations of two or more thereof. Among them, mannitol is more preferable. The amount of the sugar alcohol is preferably 0.1 to 1.0% (w/v). If the amount is below this range, there may be no effect of increasing stability. On the other hand, if the amount is above this range, there may be a problem with an increased osmotic pressure.

Some stabilizers, for example, sugar-alcohol and the like, are not limited to the literal meaning of term itself, but, in some cases, are also intended to take on other roles for preparation of aqueous formulation according to the present invention, for example, a role as isotonic reagent.

The isotonic reagent, used as another component in the aqueous formulation of the present invention, serves to maintain the osmotic pressure when erythropoietin is administered into a body in the form of solution, and also has an additional effect of further stabilizing erythropoietin in the form of solution. A representative example of isotonic reagent includes water-soluble inorganic salts, and these salts include, for example, sodium chloride, calcium chloride, sodium sulfate, etc. These salts can be used alone or in combinations of two or more thereof, and among them, sodium chloride is more preferable. The amount of water-soluble inorganic salt is preferably 0.001 to 0.7% (w/v) and may be appropriately adjusted to allow the aqueous formulation, containing various components as described above, to be isotonic.

The combination of the above stabilizers with the isotonic reagent, which are contained in an aqueous formulation, stabilizes erythropoietin in solution in the synergistic manner but not competitive manner to one another. According to the study of the inventors of the present invention, it was found that, for example, while propylene glycol has the effect of stabilizing erythropoietin in solution to a certain extent even when used alone, the stability effect can be further increased when it is used in combination with neutral amino acids. It was also found that using neutral amino acids together with stabilizers except polypropylene glycol results in less stability effect than using neutral amino acids together with stabilizers including polypropylene glycol. Therefore, in case of omitting any one of the stabilizers or isotonic reagents as mentioned above, the remarkably decreased stability of erythropoietin is resulted. This was proved by Examples and Comparative Examples to be illustrated later.

In the aqueous formulations of the present invention, the buffering reagent serves to maintain pH of the solution for stabilization of erythropoietin. The preferable example of the buffer reagent includes phosphate buffer, citrate buffer and the like, and among them, phosphate buffer is more preferable. For example, the concentration range of phosphate composing a phosphate buffer reagent is preferably between 5~50 mM and pH range of the solution is preferably between about 6.0~8.0, with about 6.5~7.5 being more preferred.

In the aqueous formulation of the present invention, any other substances or materials, as known in the art, may be selectively contained, besides stabilizers, isotonic reagent and buffering reagent, within the range of not impairing the effects of the invention.

Exemplary formulations of the present invention will be illustrated below in more detail, however, the exemplary formulations below are only the examples of the present invention, therefore, the present invention is not restricted by examples below.

Example 1

Preparation of Aqueous Formulation of Human Erythropoietin-1

An isotonic solution was prepared by adding 0.003% polysorbate 20, 0.1% propylene glycol, 1.5% glycine, 0.1% sodium chloride and 1.0% mannitol to 10 mM phosphate buffer solution, and erythropoietin (LG Life Science Co., Ltd.) was added to about 4000 IU/ml. 2 ml aliquots of the prepared solution were carefully transferred into a 3 ml glass vials and sealed, then stored at 25° C. and 37° C., respectively.

Comparative Example 1

Preparation of Aqueous Formulation of Human Erythropoietin without Additives

Erythropoietin was added in an amount of 4000 IU/ml into 10 mM phosphate buffer solution. 2 ml aliquots of the prepared solution were carefully transferred into a 3 ml glass vials and sealed, then stored at 25° C. and 37° C., respectively.

Comparative Example 2

Preparation of Aqueous Formulation of Human Erythropoietin Containing only Polysorbate 20

Erythropoietin was added in an amount of 4000 IU/ml into 10 mM phosphate buffer solution containing 0.003% polysorbate 20. 2 ml aliquots of the prepared solution were carefully transferred into a 3 ml glass vials and sealed, then stored at 25° C. and 37° C., respectively.

Comparative Example 3

Preparation of Aqueous Formulation of Human Erythropoietin without Prophyleneglycol An isotonic solution was prepared by adding 0.003% polysorbate 20, 1.5% glycine, 0.1% sodium chloride and 1.0% mannitol to 10 mM phosphate buffer solution, and erythropoietin was added to about 4000 IU/ml. 2 ml aliquots of the prepared solution were carefully transferred into a 3 ml glass vials and sealed, then stored at 25° C. and 37° C., respectively.

Comparative Example 4

Preparation of Aqueous Formulation of Human Erythropoietin without Glycine

An isotonic solution was prepared by adding 0.003% polysorbate 20, 0.5% propylene glycol, 0.1% sodium chloride and 1.0% mannitol to 10 mM phosphate buffer solution, and erythropoietin was added to about 4000 IU/ml. 2 ml aliquots of the prepared solution were carefully transferred into a 3 ml glass vials and sealed, then stored at 25° C. and 37° C., respectively.

Comparative Example 5

Preparation of Aqueous Formulation of Human Erythropoietin without Sodium Chloride An isotonic solution was prepared by adding 0.003% polysorbate 20, 1.7% glycine, 0.5% propylene glycol and 1.0% mannitol to 10 mM phosphate salt solution, and erythropoietin was added to about 4000 IU/ml. 2 ml aliquots of the prepared solution were carefully transferred into a 3 ml glass vials and sealed, then stored at 25° C. and 37° C., respectively Comparative Example 6

Preparation of Aqueous Formulation of Human Erythropoietin without Mannitol

An isotonic solution was prepared by adding 0.003% polysorbate 20, 0.5% propylene glycol, 1.5% glycine and 0.1% sodium chloride to 10 mM phosphate buffer solution, and erythropoietin was added to about 4000 IU/ml. 2 ml aliquots of the prepared solution were carefully transferred into a 3 ml glass vials and sealed, then stored at 37° C.

Experimental Example 1

Stability of Aqueous Formulations of Human Erythropoietin

The ratio of monomer and dimer of erythropoietin from aqueous formulations of Example 1 and Comparative Examples 1 to 6 was determined using SEC-HPLC following storage for 3 and 5 weeks, respectively. The result is described in TABLE 1 below.

TABLE 1

| | Recovery Yield (%) | | | | Dimer (%) | | | |
|---|---|---|---|---|---|---|---|---|
| | 25° C. | | 37° C. | | 25° C. | | 37° C. | |
| | 3 week | 5 week | 3 week | 5 week | 3 week | 5 week | 3 week | 5 week |
| Ex. 1 | 100 | 98.9 | 94.2 | 93.5 | 0.0 | 0.0 | 0.0 | 0.0 |
| Com Ex. 1 | 87.1 | 86.5 | 78.6 | 75.6 | 0.0 | 0.0 | 0.0 | 0.0 |
| Com Ex. 2 | 91.1 | 92.4 | 83.4 | 82.6 | 0.0 | 0.0 | 11.0 | 13.1 |
| Com Ex. 3 | 93.4 | 93.0 | 85.5 | 83.7 | 0.0 | 0.0 | 7.2 | 9.8 |
| Com Ex. 4 | 94.1 | 93.5 | 87.2 | 85.1 | 0.0 | 0.0 | 4.3 | 6.5 |
| Com Ex. 5 | 95.2 | 94.8 | 90.2 | 88.3 | 0.0 | 0.0 | 1.35 | 2.4 |
| Com Ex. 6 | — | — | 85.1 | 81.1 | — | — | 8.3 | 5.5 |

As can be seen in TABLE 1 above, Example 1, as an aqueous formulation of erythropoietin according to the present invention, showed a recovery yield of more than 92% following storage for 5 weeks at 37° C., with no detection of dimers. On the other hand, Comparative Example 2, containing only polysorbate 20 in the formulation, showed a high yield compared to addictive-free Comparative Example 1, but dimmers were detected. In Comparative Examples 3 to 6, not containing any one of components according to the present invention in the formulation, dimers were detected at 37° C., 3 weeks, and the recovery yield decreased to about 80%. Furthermore, in Comparative Examples 3 and 4, not containing propylene glycol and glycine in the formulation, respectively, the recovery yield is low compared to the formulation of Example 1, and many dimmers were detected. From the above results, it was confirmed that propylene glycol and the other stabilizers and isotonic reagent provided by the present invention have synergystic effects when used in combination thereof. It can be seen that while each of these components added in the formulation of the present invention has stabilizing effect, the anti-adhesion of erythropoietin in solution and stability of aqueous erythropoietin can be synergystically improved by combined effects of each ingredient.

Example 2

Preparation of Aqueous Formulation of Human Erythropoietin-2

An isotonic solution was prepared by adding 0.01% polysorbate 20, 0.1% propylene glycol, 0.1% glycine, 0.55% sodium chloride and 1.0% mannitol to 10 mM phosphate buffer solution, and erythropoietin was added to about 4000 IU/ml. 0.5 ml aliquots of the prepared solution were collected into 1 ml pre-filled syringe (Becton-Dickinson) and stored at 40° C. for 4 weeks.

Comparative Example 7

Preparation of Aqueous Formulation of Human Erythropoietin without Prophyleneglycol and Mannitol To a solution containing 4.38 mg/ml Sodium Chloride, 1.16 mg/ml monosodiumphosphate (dihydrate), 2.23 mg/ml disodiumphosphate (dihydrate), 5 mg/ml glycine, and 0.3 mg/ml polysorbate 80, added was erythropoietin to about 4000 IU/ml. 0.5 ml aliquots of the prepared solution were collected into 1 ml pre-filled syringe (Becton-Dickinson) and stored at 40° C. for 4 weeks.

Experimental Example 2

Stability of Aqueous Formulations of Human Erythropoietin-2

The purity and recovery yield of erythropoietin from the aqueous formulations of Example 2 and Comparative Example 7 were determined using SEC-HPLC at 0, 1, 3 and 4 weeks, respectively. The result is described in TABLE 2 below.

TABLE 2

| | Recovery Yield of Monomer (%) | | | |
|---|---|---|---|---|
| | 0 week | 1 week | 3 weeks | 4 weeks |
| Ex. 2 | 100.0 | 95.8 | 89.9 | 92.9 |
| Com Ex. 7 | 100.0 | 93.9 | 85.2 | 86.4 |

As seen in TABLE 2 above, the formulation of the present invention showed a high recovery yield of 92.9% after incubation of 4 weeks, compared to 86.4% for the reference formulation. Thus, it is found that the formulation of the present invention improves the stability of erythropoietin in solution.

Comparative Examples 9~13

Preparation of Various Aqueous Formulation of Human Erythropoietin

The aqueous formulations of TABLE 3 below, differing in some components from the aqueous formulations in Example 1, were prepared and stored at 25° C. and 37° C., respectively, under the same conditions as Example 1.

TABLE 3

| | Composition of the formulations |
|---|---|
| Com Ex. 9 | EPO 4000 IU/ml in PB, 0.5% PG, 0.003% Tween 20, 0.5 mM Sucrose, 1 mg/ml NaCl |
| Com Ex. 10 | EPO 4000 IU/ml in Tris, 0.5% PG, 0.003% Tween 20, 1.5% Gly, 1 mg/ml NaCl |
| Com Ex. 11 | EPO 4000 IU/ml in PB, 0.5% PVP 15K, 0.003% Tween 20, 1.5% Gly, 0.1% NaCl, 1% Mannitol |
| Com Ex. 12 | EPO 4000 IU/ml in PB, 0.5% PG, 0.003%, Tween 20, 1.5% Gly, 1 mg/ml NaCl, 0.00001% Carboxymethylcellulose |
| Com Ex. 13 | EPO 2000 IU/ml in PB, 2% PG, 2% Glucose, 0.002% Lecithin, 0.001% Tween 20 |

PB: phosphate buffer
PG: propylene glycol
PVP: polyvinylpyrrolidone

Experimental Example 3

Stability of Aqueous Formulations of Human Erythropoitin-3

The ratio of monomer and dimer of erythropoietin from the aqueous formulations of Comparative Examples 9~13 was determined using SEC-HPLC at 3 and 5 weeks, respectively. The result is described in TABLE 4 below, compared with the results of the aqueous formulations of Example 1.

TABLE 5

| | Recovery yield (%) | | | | Dimer (%) | | | |
|---|---|---|---|---|---|---|---|---|
| | 25° C. | | 37° C. | | 25° C. | | 37° C. | |
| | 3 week | 5 week | 3 week | 5 week | 3 week | 5 week | 3 week | 5 week |
| Ex. 1 | 100 | 98.9 | 94.2 | 93.5 | 0.0 | 0.0 | 0.0 | 0.0 |
| Com Ex. 9 | NA | NA | 68.1 | 72.9 | NA | NA | 5.8 | 12.5 |
| Com Ex. 10 | NA | NA | 48.2 | —* | NA | NA | 21.0 | —* |
| Com Ex. 11 | —** | —** | —** | —** | —** | —** | —** | —** |
| Com Ex. 12 | —*** | —*** | —*** | —*** | —*** | —*** | —*** | —*** |
| Com Ex. 13 | NA | NA | NA | NA | 46.6 | 56.6 | 59.2 | 58.9 |

*stop test for precipitation.
**stop test for precipitation after preparation of the formulations.
***stop test for precipitation after preparation of the formulations.
NA: not applicable.

Comparative Example 13: results obtained at 30° C. and 50° C.

As seen in TABLE 4 above, desired results were not obtained when some components in the aqueous formulations of Example 1 according to the present invention were replaced with other compounds.

Example 3

Preparation of Aqueous Formulation of Human Erythropoietin-3

For preparation of the aqueous formulations using polyhydric alcohols other than propylene glycol, the aqueous formulations of human erythropoietin were prepared in the same manner as Example 1, except for using 0.025% PEG 300 (polyethylene glycol, Mn=300) instead of propylene glycol. The prepared solution was put into a glass vial and sealed, then stored at 37° C.

Experimental Example 4

Stability of Aqueous Formulation of Human Erythropoietin-4

The ratio of monomer and dimmer of erythropoietin from the aqueous formulations of Example 3 was determined using SEC-HPLC at 3 and 5 weeks, respectively. For comparison, the aqueous formulation of Comparative Example 3, not containing polyhydric alcohol, was also tested and the results are disclosed in TABLE 5.

TABLE 5

| | Recovery Yield (%) | | Dimer (%) | |
|---|---|---|---|---|
| | 3 weeks | 5 weeks | 3 weeks | 5 weeks |
| Ex. 3 | 100.0 | 97.2 | 0.0 | 0.0 |
| Com Ex. 3 | 85.5 | 83.7 | 7.2 | 9.8 |

As seen in TABLE 5 above, Example 3, which is an aqueous formulation of erythropoietin according to the present invention using polyethylene glycol as a polyhydric alcohol, has 97% recovery yield of monomers, and no dimmers are detected. This result differs greatly from the aqueous formulation of Comparative Example 3 not using polyhydric alcohol.

Example 4

Stability of Aqueous Formulation of High Concentration of Erythropoietin

An isotonic solution was prepared by adding 0.003% polysorbate 20, 0.1% propylene glycol, 1.5% glycine, 1.0% mannitol and 0.1% sodium chloride to 10 mM phosphate buffer solution, and erythropoietin was added to about 12000 IU/ml. 0.5 ml aliquots of the prepared solution were collected into a 1 ml pre-filled syringe (Becton-Dickinson) and stored at 5° C., 25° C. and 40° C. for 3 months, respectively.

Experiment Example 5

Stability of Aqueous Formulations of High Concentration of Erythropoietin

To confirm the stability of the aqueous formulations of high concentration erythropoietin, the recovery yield and purity of the formulation prepared in Example 3 were determined after storage for 0, 6 and 12 months of storage at 5° C., and after storage for 2, 4 and 6 months at 25° C., and after storage for 1, 2 and 3 months at 40° C., respectively, using SEC-HPLC and RP-HPLC. The degree of physiological activity was evaluated by administering the formulations into B6D2F1 mice, and measuring the increase of reticulocytes. The results are disclosed in TABLE 6 above.

TABLE 6

| | Storage at 5° C. | | | Storage at 25° C. | | | Storage at 40° C. | | |
|---|---|---|---|---|---|---|---|---|---|
| | Storage term (month) | | | | | | | | |
| | 0 | 6 | 12 | 2 | 4 | 6 | 1 | 2 | 3 |
| Recovery yield (%) | 100.0 | 107.8 | 104.9 | 100.0 | 100.0 | 103.9 | 100.0 | 96.1 | 94.1 |
| Purity (%) | 100.0 | 99.9 | 99.9 | 100.0 | 99.8 | 99.3 | 99.8 | 99.3 | 99.2 |
| Physiological activity (%) | 89.7 | 90.8 | NT | 90.4 | 90.8 | 93.8 | 105.3 | 82.8 | 91.8 |

As seen in TABLE 6 above, the high concentration of erythropoetin in aqueous formulations showed the full recovery yield, purity and physiological activity until storage for 12 months at 5° C., and also until storage for 6 months at 25° C. Further, 94% of recovery yield was seen until storage for 3 months at 40° C., with little decrease in the purity and physiological activity. Therefore, the formulations according to Example 2 were confirmed to be very stable.

Experimental Example 6

Stable in Dependance on pH Effects 0.003% polysorbate 20, 0.5% propylene glycol, 1.5% glycine, 1.0% mannitol and 0.1% sodium chloride were added to 10 mM phosphate buffer solution, and erythropoietin was added to 4000 IU/ml, and then the pH was adjusted using acetate and sodium hydroxide. The prepared solution was aliquoted by 2 ml into 3 ml test tubes and sealed and subjected to storage at 40° C. for 3 weeks, and then the ratio of monomer and dimer of erythropoietin was measured. The result is described in TABLE 7 below.

TABLE 7

| pH | Recovery yield (%) | Dimer (%) |
|---|---|---|
| 6.0 | 94.4 | 0.0 |
| 6.5 | 95.2 | 0.0 |
| 7.0 | 94.3 | 0.0 |
| 7.5 | 90.3 | 0.0 |
| 8.0 | 81.7 | 0.0 |
| 8.5 | 69.8 | 0.0 |
| 9.0 | 55.3 | 11.8 |

As seen in TABLE 7 above, the recovery yield of monomer was over 90% even after 3 weeks storage at 40° C. in case of pH 6.0 to 7.5. From this result, it can be seen that the aqueous formations of erythropoietin according to the present invention, containing a non-ionic surfactant, propylene glycol, neutral amino acid, sodium chloride and isotonic reagent, are very stable at pH 6.0~7.5.

INDUSTRIAL APPLICABILITY

As described above, the aqueous formulation of erythropoietin according to the present invention, containing human erythropoietin and non-ionic surfactant, polyhydric alcohol, neutral amino acid, sugar alcohol as a stabilizer, isotonic reagent and buffer reagent, improves the problem of decreased physiological activity due to denaturation upon long-term storage in solution; and in addition, has the effects of preventing erythropoietin proteins from adhering to ampoule walls.

Other examples and uses of the invention will be apparent to those skilled in the art from consideration of the specification and practice of the invention disclosed herein. It is intended that the specification and examples be considered as exemplary only, with the scope of particular examples of the invention indicated by the following claims.

What is claimed is:

1. An aqueous formulation of human erythropoietin, comprising:
   the human erythropoietin;
   a non-ionic surfactant;
   0.001 to 0.1% (w/v) of a polyhydric alcohol;
   a neutral amino acid;
   0.1 to 1.0% (w/v) of mannitol;
   a water-soluble inorganic salt; and
   a buffering reagent.

2. The aqueous formulation of human erythropoietin according to claim 1, wherein said human erythropoietin is native or recombinant erythropoietin.

3. The aqueous formulation of human erythropoietin according to claim 1, wherein said non-ionic surfactant is a polysorbate-based non-ionic surfactant or poloxamer-based non-ionic surfactant or a combination thereof;
   said polyhydric alcohol is one or more selected from the group consisting of propylene glycol, polyethylene glycol of a low molecular weight, glycerol and polypropylene glycol of a low molecular weight;
   said neutral amino acid is one or more selected from the group consisting of glycine, alanine, leucine and isoleucine;
   said water-soluble inorganic salt is one or more selected from the group consisting of sodium chloride, calcium chloride and sodium sulfate; and
   said buffering reagent is one or more selected from the group consisting of a phosphate buffer and citrate buffer.

4. The aqueous formulation of human erythropoietin according to claim 3, wherein said non-ionic surfactant is a polysorbate 20, said polyhydric alcohol is propylene glycol, said neutral amino acid is glycine, said water-soluble inorganic salt is sodium chloride, and said buffering reagent is the phosphate buffer.

5. The aqueous formulation of human erythropoietin according to claim 1, wherein the content of non-ionic surfactant is in the range of 0.0001 to 0.01% (w/v).

6. The aqueous formulation of human erythropoietin according to claim 1, wherein the content of neutral amino acid is in the range of 0.001 to 2% (w/v).

7. The aqueous formulation of human erythropoietin according to claim 1, wherein the content of said water-soluble inorganic salt is in the range of 0.001 to 0.7% (w/v).

8. The aqueous formulation of human erythropoietin according to claim 1, wherein the concentration of salt in the buffering reagent is in the range of 1 mM to 50 mM, and pH thereof is in the range of 6.0 to 7.5.

9. The aqueous formulation of human erythropoietin according to claim 1, wherein the content of erythropoietin is in the range of 100 IU/ml to 120,000 IU/ml.

* * * * *